United States Patent
Kawamura

(10) Patent No.: US 10,383,860 B2
(45) Date of Patent: Aug. 20, 2019

(54) PHARMACEUTICAL COMPOSITION COMPRISING RAPAMYCIN OR DERIVATIVE THEREOF, AND METHOD FOR PRODUCING THE SAME

(71) Applicant: NIPPON KAYAKU KABUSHIKI KAISHA, Tokyo (JP)

(72) Inventor: Dai Kawamura, Saitama (JP)

(73) Assignee: NIPPON KAYAKU KABUSHIKI KAISHA, Tokyo (JP)

(*) Notice: Subject to any disclaimer, the term of this patent is extended or adjusted under 35 U.S.C. 154(b) by 0 days.

(21) Appl. No.: 15/747,604

(22) PCT Filed: Jul. 27, 2016

(86) PCT No.: PCT/JP2016/071957
§ 371 (c)(1),
(2) Date: Jan. 25, 2018

(87) PCT Pub. No.: WO2017/018433
PCT Pub. Date: Feb. 2, 2017

(65) Prior Publication Data
US 2018/0214423 A1    Aug. 2, 2018

(30) Foreign Application Priority Data

Jul. 28, 2015 (JP) ................................. 2015-148978
Jan. 6, 2016 (JP) ................................. 2016-000766

(51) Int. Cl.
| A61K 31/436 | (2006.01) |
| A61K 47/26 | (2006.01) |
| A61K 9/14 | (2006.01) |
| A61K 47/38 | (2006.01) |
| A61K 31/7016 | (2006.01) |

(52) U.S. Cl.
CPC .............. *A61K 31/436* (2013.01); *A61K 9/14* (2013.01); *A61K 47/26* (2013.01); *A61K 47/38* (2013.01); *A61K 31/7016* (2013.01); *A61K 2300/00* (2013.01)

(58) Field of Classification Search
CPC .. A61K 31/436; A61K 31/7016; A61K 47/26; A61K 47/38; A61K 9/14; C08C 19/08; C08J 11/20; C08J 2319/00; C08J 2321/00
See application file for complete search history.

(56) References Cited

U.S. PATENT DOCUMENTS

| 2009/0155929 A1 | 6/2009 | Wie et al. |
| 2010/0316724 A1 | 12/2010 | Whitfield et al. |
| 2011/0136136 A1 | 6/2011 | Wie et al. |
| 2012/0064546 A1 | 3/2012 | Wei et al. |
| 2014/0242162 A1* | 8/2014 | Diederich ............ A61K 9/2072 424/461 |
| 2015/0265582 A1* | 9/2015 | Armer ................ A61K 31/4196 424/451 |
| 2015/0328159 A1 | 11/2015 | Whitfield et al. |
| 2016/0303240 A1* | 10/2016 | Oki ...................... A61K 31/573 |

FOREIGN PATENT DOCUMENTS

| JP | H11-509223 A | 8/1999 |
| JP | 2000-159788 A | 6/2000 |
| JP | 2002-531527 A | 9/2002 |
| JP | 2005-507897 A | 3/2005 |
| JP | 2014-528431 A | 10/2014 |
| WO | 97/03654 A2 | 2/1997 |
| WO | 00/33878 A2 | 6/2000 |
| WO | 03/028705 A1 | 4/2003 |
| WO | 2009/079374 | 6/2009 |
| WO | 2010/130982 | 11/2010 |
| WO | 2013/022201 A1 | 2/2013 |
| WO | 2013/050419 A1 | 4/2013 |
| WO | 2014/075554 | 5/2014 |
| WO | 2015/099029 | 7/2015 |

OTHER PUBLICATIONS

Ohtake et al. (J of Pharmaceutical Sciences, 100, 6, May 2011). (Year: 2011).*
Markus Hofer et al., "Recombinant spider silk particles for controlled delivery of protein drugs", Biomaterials, vol. 33, pp. 1554-1562. 2012.
M.S. Kang et al., "Development of a stabilizer for lyophilization of an attenuated duck viral hepatitis vaccine", Poultry Science, vol. 89, pp. 1167-1170, 2010.
International Search Report from Patent Application No. PCT/JP2016/071957, dated Oct. 18, 2016.
International Preliminary Report on Patentability from Patent Application No. PCT/JP2016/071957, dated Jan. 30, 2018.
Extended European Search Report, dated Feb. 20, 2019 in European patent Application No. 16830538.1.

* cited by examiner

*Primary Examiner* — Umamaheswari Ramachandran
(74) *Attorney, Agent, or Firm* — Greenblum & Bernstein, P.L.C.

(57) ABSTRACT

It is an object of the present invention to provide a pharmaceutical composition which can suppress a reduction in the content of an active ingredient caused by oxidation or decomposition of the rapamycin or a derivative thereof, can ensure long-term stability, and has high safety. The present invention provides a pharmaceutical composition comprising (A) rapamycin or a derivative thereof and (B) trehalose, and a method for producing a pharmaceutical composition comprising rapamycin or a derivative thereof, which comprises adding a solution containing rapamycin or a derivative thereof to sugars having a critical relative humidity at 25° C. of 95% or more.

9 Claims, No Drawings

PHARMACEUTICAL COMPOSITION COMPRISING RAPAMYCIN OR DERIVATIVE THEREOF, AND METHOD FOR PRODUCING THE SAME

TECHNICAL FIELD

The present invention relates to a pharmaceutical formulation composition comprising rapamycin or a derivative thereof, the stability of which has been improved. Since rapamycin or a derivative thereof is extremely instable to oxygen, light and moisture, it is problematic in terms of preservation stability. The present invention is a technique relating to a pharmaceutical formulation composition, in which the preservation stability of such a compound has been improved by a stabilizer having excellent safety with consideration to in vivo administration. Moreover, with regard to the preservation stability of such a compound, the present invention relates to a technique of optimizing components of a pharmaceutical composition and a production method thereof, so as to provide a pharmaceutical formulation composition having more excellent long-term stability than pharmaceutical compositions obtained by any previously reported production methods.

BACKGROUND ART

It has been known that rapamycin (sirolimus) is a macrolide antibiotic discovered from the metabolite of actinomyces and has an immunosuppressive action. Rapamycin has an action to inhibit a mammalian rapamycin target protein (mammalian target of rapamycin; mTOR) that regulates cell division, cell growth, survival, etc. This mTOR is a main serine-threonine kinase, which regulates the synthesis of proteins by stimulation with growth factors, nutrients, etc., and the mTOR has been known to regulate the growth, proliferation and survival of cells, and angiogenesis. Hence, the mTOR inhibitory action of rapamycin has been focused, and the synthesis of a derivative thereof has been attempted. As a result, everolimus and temsirolimus have been discovered as antitumor agents.

A pharmaceutical formulation used to provide a pharmaceutical product comprising rapamycin or a derivative thereof has been reported. Patent Literature 1 discloses that a solution containing a mixture of rapamycin, hydroxypropylmethyl cellulose, lactose and the like is prepared, the solvent is then distilled away from the solution, and the obtained solid dispersion is then formulated. In addition, Patent Literature 2 discloses a tablet comprising everolimus used as a rapamycin, crospovidone used as a disintegrator, colloidal silicon dioxide, and lactose.

Rapamycin or a derivative thereof has been known to have physical properties by which it is easily oxidized and is extremely instable. Hence, in general, an antioxidant is added to a pharmaceutical product formulation comprising, as an active ingredient, rapamycin. For instance, to a rapamycin preparation (registered trademark: Rapalimus) and a temsirolimus preparation (registered trademark: Torisel), tocopherol is added. In addition, for everolimus formulations (registered trademark: Afinitor and Certican), a synthetic antioxidant, dibutylhydroxytoluene (BHT) is used.

Regarding a method of efficiently stabilizing a rapamycin derivative using an antioxidant, Patent Literature 3 discloses that a mixed solution containing everolimus and BHT as a synthetic antioxidant is prepared, and the solvent is then removed from the mixed solution, so as to obtain a stabilized everolimus solid. Examples of the antioxidant used in this publication include BHT, tocopherol and ascorbic acid.

However, it has been reported that BHT used as a synthetic antioxidant exhibits carcinogenicity or reproduction toxicity, and thus, this is a chemical substance, the amount used of which is limited. On the other hand, tocopherol has higher safety than BHT, but its antioxidative activity is lower than that of BHT. Thus, the effect of tocopherol to stabilize rapamycin based on its antioxidative action has a certain limit.

As other antioxidants used as additives for pharmaceutical products, there have been known ascorbic acid, and ascorbyl palmitate as a fat-soluble derivative of ascorbic acid. Since these antioxidants also have antioxidative effects that are inferior to those of synthetic antioxidants such as BHT, they are insufficient to be applied to pharmaceutical formulations comprising rapamycin.

Meanwhile, Patent Literature 4 discloses that an ethanol solution of everolimus is added to a water-soluble polymer such as hypromellose, and the mixture is then granulated to prepare a solid dispersion, thereby obtaining a stable everolimus composition, without using antioxidants.

PRIOR ART LITERATURES

Patent Literatures

Patent Literature 1: JP Patent Publication (Kohyo) No. 11-509223 A (1999)

Patent Literature 2: JP Patent Publication (Kohyo) No. 2005-507897 A

Patent Literature 3: JP Patent Publication (Kohyo) No. 2002-531527 A

Patent Literature 4: International Publication No. WO 2013/022201

SUMMARY OF INVENTION

Object to be Solved by the Invention

It is an object of the present invention to provide a pharmaceutical composition used in a pharmaceutical formulation comprising rapamycin or a derivative thereof, wherein the pharmaceutical composition can suppress a reduction in the content of an active ingredient caused by oxidation or decomposition of the rapamycin or a derivative thereof, can ensure long-term stability, and has high safety. It is another object of the present invention to provide a method for producing a pharmaceutical composition used in a pharmaceutical formulation comprising rapamycin or a derivative thereof, wherein the pharmaceutical composition can suppress a reduction in the content of an active ingredient caused by oxidation or decomposition of the rapamycin or a derivative thereof, and can ensure long-term stability. It is a further object of the present invention to provide a pharmaceutical formulation comprising rapamycin or a derivative thereof, which can ensure long-term stability under conditions where it is distributed and preserved as a pharmaceutical product.

Means for Solving the Object

The present inventors have found that the oxidation or decomposition of rapamycin or a derivative thereof comprised in a pharmaceutical formulation comprising the rapamycin or a derivative thereof can be suppressed by using trehalose as an additive, thereby completing the present invention. Specifically, the present application includes the invention according to the following [1] to [9] as features.

[1] A pharmaceutical composition comprising (A) rapamycin or a derivative thereof and (B) trehalose.

In the present invention, by combining rapamycin or a derivative thereof with trehalose to produce a pharmaceutical composition, a composition comprising rapamycin or a derivative thereof, the stability of which has been improved, can be produced.

[2] The pharmaceutical composition according to the above [1], which is produced by preparing a solution containing (A) rapamycin or a derivative thereof and (B) trehalose, and then removing the solvent from the solution.

As an aspect of mixing rapamycin or a derivative thereof with trehalose, it is preferable to prepare a solution containing both of the substances and then to obtain a solid mixture from the solution. Such a solid mixture is a mixture formed by associating rapamycin or a derivative thereof with trehalose at a molecular level, and thus, it is difficult to explain this solid mixture with a chemical structure, properties, etc. Hence, it is appropriate that a more detailed aspect of the pharmaceutical composition comprising (A) rapamycin or a derivative thereof and (B) trehalose according to the present invention is expressed as a solid mixture comprising rapamycin or a derivative thereof and trehalose, which is specified by the production method according to the above [2], and this pharmaceutical composition is considered to satisfy the requirements regarding the clarity of the invention.

[3] The pharmaceutical composition according to the above [1] or [2], which comprises 0.1 to 100.0 parts by mass of (B) the trehalose, based on 1 part by mass of (A) the rapamycin or a derivative thereof.

[4] The pharmaceutical composition according to any one of the above [1] to [3], which further comprises an antioxidant.

In order to suppress a reduction in the content of rapamycin or a derivative thereof in the pharmaceutical composition of the present invention, which is caused by oxidation of the rapamycin or a derivative thereof, an antioxidant may be further added to the present pharmaceutical composition.

[5] The pharmaceutical composition according to any one of the above [1] to [4], which comprises a cellulose derivative and/or sugars.

[6] A pharmaceutical formulation comprising the pharmaceutical composition according to any one of the above [1] to [5].

Moreover, the present application also includes a method for producing a pharmaceutical composition comprising rapamycin or a derivative thereof and trehalose as a feature of the invention.

[7] A method for producing a pharmaceutical composition comprising rapamycin or a derivative thereof, which comprises preparing a solution containing (A) rapamycin or a derivative thereof and (B) trehalose, and then removing the solvent from the solution.

According to the above-described production method, a solid mixture, in which rapamycin or a derivative thereof is associated with trehalose at a molecular level, can be produced. Furthermore, when an antioxidant is used, such an antioxidant may be added upon preparation of the solution, or may also be added to the solid mixture.

[8] A method for producing a pharmaceutical formulation comprising rapamycin or a derivative thereof, which comprises preparing a solution containing (A) rapamycin or a derivative thereof and (B) trehalose, then adding a cellulose derivative and/or sugars to the prepared solution, and then removing the solvent from the mixture.

[9] A method for producing a pharmaceutical formulation comprising rapamycin or a derivative thereof, which comprises preparing a solution containing (A) rapamycin or a derivative thereof and (B) trehalose, then removing the solvent from the prepared solution to obtain a pharmaceutical composition comprising the rapamycin or a derivative thereof, and then adding a cellulose derivative and/or sugars to the pharmaceutical composition.

Upon production of a pharmaceutical formulation comprising rapamycin or a derivative thereof, such as the production method according to the above [8] or [9], the cellulose derivative and/or sugars used as pharmaceutical additives may be added at the stage of preparing a solid mixture, in which rapamycin or a derivative thereof is associated with trehalose at a molecular level, or may also be added after preparation of the solid mixture.

Further, the present inventors have found that a pharmaceutical composition comprising rapamycin or a derivative thereof, which has been produced by adding a solution of rapamycin or a derivative thereof dropwise to sugars having a critical relative humidity at 25° C. of 95% or more, and then removing the solvent from the mixture, exhibits the effect of stabilizing rapamycin or a derivative thereof for a long period of time, thereby completing the present invention. Specifically, the present application includes the invention according to the following [10] to [16] as features.

[10] A method for producing a pharmaceutical composition comprising rapamycin or a derivative thereof, which comprises adding a solution containing rapamycin or a derivative thereof to sugars having a critical relative humidity at 25° C. of 95% or more.

The present invention relates to a method for producing a pharmaceutical composition, which comprises adding a solution containing rapamycin or the like that is an active ingredient of a pharmaceutical product to sugars that is in a solid state and hardly exhibits absorbency, and then mixing them. The pharmaceutical composition obtained by the present production method is a pharmaceutical composition that can suppress decomposition of the rapamycin or a derivative thereof comprised as an active ingredient and thus can be excellent in terms of preservation stability.

[11] The method for producing a pharmaceutical composition according to the above [10], wherein the content of the sugars having a critical relative humidity at 25° C. of 95% or more is 0.5 to 50 parts by mass based on 1 part by mass of the rapamycin or a derivative thereof.

[12] The method for producing a pharmaceutical composition according to the above [10] or [11], wherein the solution containing rapamycin or a derivative thereof comprises a stabilizer.

[13] The method for producing a pharmaceutical composition according to any one of the above [10] to [12], wherein the solution containing rapamycin or a derivative thereof comprises a water-soluble polymer carrier.

[14] The method for producing a pharmaceutical composition according to any one of the above [10] to [13], wherein the solution containing rapamycin or a derivative thereof comprises a water-soluble cellulose derivative.

In the production method of the present invention, by adding a stabilizer or a water-soluble polymer carrier such as a water-soluble cellulose derivative to the solution containing rapamycin or a derivative thereof, the effect of suppressing decomposition of rapamycin or the like can be further improved, and a pharmaceutical composition excellent in terms of stability can be provided.

[15] A pharmaceutical composition comprising rapamycin or a derivative thereof, which is produced by adding a solution containing rapamycin or a derivative thereof to sugars having a critical relative humidity at 25° C. of 95% or more.

The present invention relates to a pharmaceutical composition comprising rapamycin or a derivative thereof and the above-described sugars. A composition produced by adding such rapamycin or the like that is in the form of a solution to such sugars exhibits extremely high stability. This is a physical property different from that of a pharmaceutical composition produced by physically mixing the rapamycin or the like with the sugars, or a pharmaceutical composition produced from a solution containing the rapamycin or the like and the sugars. It is difficult to explain a more detailed aspect of the pharmaceutical composition according to the present invention with a chemical structure, properties, etc. Hence, it is appropriate that the pharmaceutical composition obtained in the present invention is expressed as a pharmaceutical composition comprising rapamycin or a derivative thereof and the above-described sugars, which is specified by the production method according to the above [15], and such a pharmaceutical composition is considered to satisfy the requirements regarding the clarity of the invention.

[16] The pharmaceutical composition according to the above [15], wherein the content of the rapamycin or a derivative thereof is at least 80% of the initial value, after the pharmaceutical composition has been preserved under light-shielded conditions at 60° C. at a relative humidity of approximately 49% for 14 days.

The pharmaceutical composition of the present invention has excellent preservation stability, and in a more preferred aspect, the pharmaceutical composition of the present invention is specified by the above-described preservation stability.

Advantageous Effects of Invention

According to the present invention described in the above [1] to [9], there can be provided a pharmaceutical composition comprising rapamycin or a derivative thereof, wherein the pharmaceutical composition can suppress a reduction in the content of an active ingredient caused by oxidation or decomposition of the rapamycin or a derivative thereof, can ensure long-term stability, and has high safety. Moreover, according to the present invention, there can also be provided a pharmaceutical formulation comprising rapamycin or a derivative thereof, wherein the pharmaceutical formulation can ensure long-term stability and has high safety. The pharmaceutical composition and pharmaceutical formulation of the present invention are pharmaceutical formulations, which avoid the use of BHT that is problematic in terms of carcinogenicity or reproduction toxicity, and these are pharmaceutical formulations comprising rapamycin or a derivative thereof, which ensure stability and safety.

According to the present invention described in the above [10] to [16], there can be produced a pharmaceutical composition comprising rapamycin or a derivative thereof, wherein the pharmaceutical composition can suppress a reduction in the content of an active ingredient caused by oxidation or decomposition of the rapamycin or a derivative thereof, and can ensure long-term stability.

Embodiments for Carrying Out the Invention

<1> Concerning a Pharmaceutical Composition Comprising Rapamycin or a Derivative Thereof and Trehalose, and a Method for Producing the Same The pharmaceutical composition of the present invention is characterized in that it comprises (B) trehalose in order to suppress oxidation or decomposition of (A) rapamycin or a derivative thereof. The details thereof will be described below.

The present invention comprises, as an active ingredient, (A) rapamycin or a derivative thereof.

Rapamycin (common name: Sirolimus) is a compound having a macrolide skeleton that has been isolated from the metabolite of actinomyces, *Streptomyces Hygroscopicus*, separated from the soil of Easter Island.

The term "rapamycin derivative" means a substance prepared by chemically modifying rapamycin used as a mother core. Examples of the rapamycin derivative include 16-O-substituted rapamycin (see, for example, WO 94/022136), 40-O-substituted rapamycin (see, for example, U.S. Pat. No. 5,258,389 and WO 94/09010), carboxylic acid ester-substituted rapamycin (see, for example, WO 92/05179), amide-substituted rapamycin (see, for example, U.S. Pat. No. 5,118,677), fluorine-substituted rapamycin (see, for example, U.S. Pat. No. 5,100,883), and acetal-substituted rapamycin (see, for example, U.S. Pat. No. 5,151,413). The rapamycin or a derivative thereof of the present invention is not limited thereto, but the aforementioned rapamycin derivatives can be used as applicable preferred compounds.

The rapamycin derivative is preferably a 40-O-substituted rapamycin derivative, in which the hydroxyl group at position 40 of the cyclohexyl group of rapamycin is substituted with a hydroxyalkyl group, a hydroxyalkoxyalkyl group, an acylaminoalkyl group, an aminoalkyl group, or a hydroxy-substituted acyl group.

The rapamycin derivative is more preferably 40-O-(2-hydroxyethyl)rapamycin (everolimus), or 40-O-[3-hydroxy-2-(hydroxymethyl)-2-methylpropanoate]rapamycin (temsirolimus).

As (A) rapamycin or a derivative thereof of the present invention, rapamycin (Sirolimus), everolimus, or temsirolimus is preferably used.

As such (A) rapamycin or a derivative thereof, a compound having a quality that can be sufficiently used as a pharmaceutical product is preferably used.

(B) Trehalose used in the present invention is a disaccharide formed by an α,α-glycoside bond between two glucose units, and it has been used as a pharmaceutical product additive or a food product additive. The (B) trehalose is not particularly limited and any compound can be used herein, as long as it is a compound having a disaccharide structure formed by an α,α-glycoside bond between two glucose units in a chemical structure thereof. Accordingly, as such (B) trehalose, a derivative thereof may also be used. Examples of the trehalose derivative include α-oligoglucosyl α,α-trehaloses such as α-maltosyl α,α-trehalose, α-maltotriosyl α,α-trehalose, α-maltotetraosyl α,α-trehalose, and α-maltopentaosyl α,α-trehalose.

In the present invention, (B) trehalose and/or a trehalose derivative may be used alone or may also be used in combination.

Trehalose is preferably used.

In the present invention, (B) trehalose may be added in an amount of 0.1 part by mass or more, based on 1 part by mass of (A) rapamycin or a derivative thereof. (B) Trehalose may be used in an amount of preferably 0.2 parts by mass or more, and more preferably 0.5 parts by mass or more. In the present invention, trehalose does not have physical properties that impair the stability of the rapamycin or a derivative thereof, and also, trehalose is not a substance, the use amount of which has a limitation as an additive to pharmaceutical products. Accordingly, the upper limit of the use amount is not particular limited, and thus, trehalose should be used herein in an amount practically usable as a pharmaceutical product.

Taking into consideration the ensuring of the stability of the rapamycin or a derivative thereof and the realistic use amount of a pharmaceutical product additive, (B) trehalose is preferably used in an amount of 0.1 to 100 parts by mass, based on 1 part by mass of (A) rapamycin or a derivative thereof. (B) Trehalose is used in an amount of more preferably 0.2 to 50 parts by mass, even more preferably 0.5 to 20 parts by mass, and further preferably 0.5 to 10 parts by mass.

The pharmaceutical composition of the present invention comprises two components, namely, (A) rapamycin or a derivative thereof and (B) trehalose. The two components are comprised in the pharmaceutical composition of the present invention without particular limitations, as long as they are mixed with each other and are present in the form of a mixture. The method of mixing the two components with each other can be a method, which comprises mixing (A) rapamycin or a derivative thereof that is in a solid state with (B) trehalose that is also in a solid state, and then mechanically blending them using optionally given mixer or the like. During the operations, a suitable solvent may be added to the components, so as to promote a dispersion of them. When the compounds (A) and (B) are mixed with each other in a solid state, it is advantageous from the viewpoint of the improvement of dispersibility that the two components are used in the form of small particles or granules having a mean particle diameter of 0.1 to 10 mm.

Alternatively, there may also be applied a method, which comprises preparing a solution containing either (A) rapamycin or a derivative thereof, or (B) trehalose, then mixing the prepared solution with the other component that is in a solid state, and then arbitrarily mechanically blending them.

In the pharmaceutical composition of the present invention, the aspect that the two components, namely, (A) rapamycin or a derivative thereof and (B) trehalose are mixed with each other and are present in the form of a mixture is preferably a solid mixture comprising (A) rapamycin or a derivative thereof and (B) trehalose, which is obtained by preparing a solution containing the two components, and then removing the solvent from the solution. Such a solid mixture is considered to be a mixture, in which the rapamycin or a derivative thereof is associated with the trehalose at a molecular level, and thus, this is a mixed form, in which the highest effect of the trehalose to stabilize the rapamycin or a derivative thereof is exhibited.

The solvent that can be used to prepare a solution containing (A) rapamycin or a derivative thereof and (B) trehalose is not limited, as long as both (A) rapamycin or a derivative thereof and (B) trehalose are dissolved therein. Examples of such a solvent include water, methanol, ethanol, 1-propanol, 2-propanol, 1-butanol, 2-butanol, 2-methyl-1-propanol, 3-methyl-1-butanol, 1-pentanol, ethylene glycol, glycerin, formic acid, acetic acid, acetone, methyl ethyl ketone, methyl isobutyl ketone, anisole, methyl acetate, ethyl acetate, ethyl formate, propyl acetate, isopropyl acetate, n-butyl acetate, isobutyl acetate, acetonitrile, t-butyl methyl ether, tetrahydrofuran, 1,4-dioxane, diethyl ether, diisopropyl ether, pentane, hexane, heptane, N,N-dimethylformamide, N,N-dimethylacetamide, N-methylpyrrolidone, 1,3-dimethyl-2-imidazolidinone, dimethyl sulfoxide, dichloromethane, and chloroform. These solvents may be used alone, or may also be used as a mixed solvent comprising two or more types of solvents. Examples of the solvent used herein are not limited thereto, but the aforementioned solvents can be used as applicable preferred solvents.

Taking into consideration the subsequent removal of a solvent it is preferable to use a solvent having a boiling point of 120° C. or lower, which can be distilled away under mild conditions. Examples of such a preferred solvent include water, methanol, ethanol, propanol, acetonitrile, acetone, methyl ethyl ketone, ethyl acetate, butyl acetate, tetrahydrofuran, 1,4-dioxane, pentane, heptane, diethyl ether, and t-butyl methyl ether.

The amount of the solvent used is not particularly limited, as long as (A) rapamycin or a derivative thereof and (B) trehalose are completely dissolved in the solvent. Hence, the amount of the solvent used can be adjusted, as appropriate.

In addition, upon preparation of the solution, the temperature is increased, as appropriate, so that dissolution of (A) rapamycin or a derivative thereof and (B) trehalose in the solvent may be promoted. The temperature of the solution upon preparation thereof is not particularly limited. Taking into consideration the stability of (A) rapamycin or a derivative thereof, it is preferable to prepare the solution at a temperature of 0° C. to 80° C.

The method of preparing a solution containing rapamycin or a derivative thereof and trehalose is not particularly limited in the present invention, as long as it is a method of dissolving both the rapamycin or a derivative thereof and the trehalose in the solution. Examples of such a method include: a method, which comprises previously mixing rapamycin or a derivative thereof with trehalose, then adding a solvent, in which the components are dissolved, to the mixture, and then dissolving the components in the solvent; and a method, which comprises mixing a solution prepared by adding a solvent to rapamycin or a derivative, with a solution prepared by adding a solvent to trehalose. The method of preparing a solution containing rapamycin or a derivative thereof and trehalose is not limited thereto, but these preparation methods can be used as applicable preferred preparation methods.

As a method of removing a solvent from a solution containing (A) rapamycin or a derivative thereof and (B) trehalose, a method of distilling the solvent away from the solution is applied. Regarding such a method of distilling the solvent away from the solution, the solvent can be removed from the solution by heating the solution. At that time, reduced pressure conditions are preferably applied because the solvent can be removed under mild temperature conditions. Otherwise, the solvent can also be removed by a spray-drying method, so as to obtain a solid mixture.

Moreover, there may also be adopted a method, which comprises precipitating a solid mixture comprising (A) rapamycin or a derivative thereof and (B) trehalose from a solution containing the components (A) and (B), and then removing the solvent according to a filtration method. Examples of the method of precipitating a solid mixture include: what is called, a recrystallization method of promoting crystallization by cooling; and what is called, a precipitation method of adding a solvent for crystallization, which is miscible with a solution containing (A) rapamycin or a derivative thereof and (B) trehalose, and in which the components (A) and (B) are insoluble or hardly-soluble, to the solid mixture, followed by crystallization.

The above-described solvent for crystallization is not particularly limited and any solvent can be applied herein, as long as it is miscible with a solution containing (A) rapamycin or a derivative thereof and (B) trehalose, and also, the components (A) and (B) are insoluble or hardly soluble therein. Examples of the solvent for crystallization include water, diethyl ether, diisopropyl ether, tetrahydrofuran, 1,4-dioxane, hexane, heptane, and toluene. The type and use amount of the solvent for crystallization may be determined, as appropriate, depending on the type and amount of a solvent used in preparation of the solution.

A solvent for crystallization is added to a solution containing (A) rapamycin or a derivative thereof and (B) trehalose, so that a solid mixture containing the components (A) and (B) is crystallized. After that, the mixture is arbitrarily cooled to promote crystallization, so as to prepare a suspension. Thereafter, the solvent is removed from the suspension by a filtration method, so as to obtain a solid mixture.

In the pharmaceutical composition of the present invention, as a stabilization adjuvant for ensuring the stability of the rapamycin or a derivative thereof, an antioxidant can be arbitrarily combined with the trehalose, and can be then used. As such an antioxidant, a known antioxidant exhibiting the effect of stabilizing the rapamycin and a derivative thereof can be used. Examples of such a known antioxidant include nitrite, ascorbic acid and a salt thereof, ascorbyl palmitate, ascorbyl stearate, sulfite, alpha-thioglycerin, edetic acid and a salt thereof, erythorbic acid and a salt thereof, cysteine hydrochloride, citric acid and a salt thereof, dichloroisocyanuric acid, dibutylhydroxytoluene, lecithin, thioglycolic acid and a salt thereof, thiomalic acid and a salt thereof, tocopherol, tocopherol acetic acid ester, pyrosulfite, butylhydroxyanisole, 1,3-butylene glycol, pentaerythritol tetrakis[3-(3,5-di-t-butyl-4-hydroxyphenyl)propionate]benzotriazole, isopropyl gallate, and 2-mercaptobenzimidazole. Examples of the antioxidant used herein are not limited thereto, but these compounds can be used as applicable preferred compounds.

The antioxidant can be used, as appropriate, in an amount that does not impair the stability of the rapamycin or a derivative thereof. When the antioxidant is used, the addition amount is not particularly limited. The antioxidant is preferably used in an amount of 0.1 to 100 parts by mass, based on 1 part by mass of (A) the rapamycin or a derivative thereof. The antioxidant is used in an amount of more preferably 0.1 to 50 parts by mass, and further preferably 0.5 to 20 parts by mass.

The above-described antioxidant is used by being added separately, to a mixture of (A) the rapamycin or a derivative thereof and (B) the trehalose. Alternatively, the antioxidant may be used by being added to a solid mixture prepared from the solution of the components (A) and (B). Otherwise, a solution containing the components (A) and (B) and an antioxidant is prepared, and the solvent is then removed from the solution, so that the antioxidant may be used in the form of a solid mixture comprising the components (A) and (B) and the antioxidant.

When the antioxidant is used in the pharmaceutical composition of the present invention, it is preferable that a solution containing (A) the rapamycin or a derivative thereof and (B) the trehalose and the antioxidant be prepared, the solvent be removed from the solution, and the antioxidant be used in the form of a solid mixture comprising the components (A) and (B) and the antioxidant. Examples of the method of removing the solvent, which is applied in the method of obtaining such a solid mixture, include a method involving distillation of the solvent and a method involving crystallization and filtration, as with the aforementioned methods. As such a solvent distillation method, a spray-drying method may also be used.

To the pharmaceutical composition of the present invention, a cellulose derivative and/or sugars may be added. These substances are used as pharmaceutical additives for preparing pharmaceutical product formulations.

The cellulose derivative is not particularly limited and any cellulose derivative can be used herein, as long as it is an additive that is commonly used in preparation of pharmaceutical product formulations. Examples of the cellulose derivative include crystalline cellulose, methyl cellulose, ethyl cellulose, cellulose acetate phthalate, low-substituted hydroxypropyl cellulose, hydroxypropyl cellulose, hydroxymethylpropyl cellulose, hydroxypropylmethyl cellulose acetate succinate, hydroxypropylmethyl cellulose, and hydroxypropylmethyl cellulose phthalate. Among these, it is preferable to use crystalline cellulose, methyl cellulose, ethyl cellulose, low-substituted hydroxypropyl cellulose, hydroxypropyl cellulose, hydroxymethylpropyl cellulose, and hydroxypropylmethyl cellulose.

Moreover, the sugars are not particularly limited and any sugars can be used herein, as long as they are additives that are commonly used in preparation of pharmaceutical product formulations. Examples of the sugars include arabinose, isomaltose, inositol, erythritol, galactosamine, galactose, xylitol, xylose, glucosamine, glucose, gentiobiose, kojibiose, sucrose, cellobiose, sophorose, sorbitol, thioglucose, turanose, deoxyribose, nigerose, palatinose, fucose, fructose, mannitol, maltose, mannose, melibiose, lactose, rhamnose, laminaribiose and trehalose. Among these, it is preferable to use lactose, mannitol, maltose, erythritol, sorbitol, fucose, xylitol, fructose, inositol, and trehalose.

The above-described cellulose derivative and/or sugars may be used alone, or in combination of multiple types.

The cellulose derivative and/or the sugars are used by being added to a pharmaceutical composition comprising (A) the rapamycin or a derivative thereof, (B) the trehalose, and optionally given antioxidant.

That is to say, the cellulose derivative and/or the sugars are used by being added to (A) the rapamycin or a derivative thereof, (B) the trehalose, and optionally given antioxidant, so as to prepare a mixture (addition method 1). Alternatively, the cellulose derivative and/or the sugars may be added to a solid mixture prepared from a solution containing the components (A) and (B) and optionally given antioxidant, so as to prepare a mixture (addition method 2).

When the cellulose derivative and/or sugars that are in a solid state are mixed with the components (A) and (B) and optionally given antioxidant that are also in a solid state, it is preferable that these components be mechanically mixed with one another using a mixer or the like, so that they are fully dispersed.

Furthermore, as an alternative method, a solution containing the components (A) and (B) and optionally given antioxidant is mixed with the cellulose derivative and/or the sugars, and the solvent is then removed from this mixture, so that a mixture consisting of a solid mixture of the components (A) and (B) and optionally given antioxidant, and the cellulose derivative and/or the sugars, may be obtained and used (addition method 3).

The above-described addition method 3 is a method of adding the cellulose derivative and/or the sugars to a solution containing the components (A) and (B) and optionally given antioxidant. In this case, the cellulose derivative and/or the sugars are not necessarily dissolved in the solution, and they may be in the state of a suspension. The solvent is removed from this mixture, so that a mixture consisting of a solid mixture of the components (A) and (B) and optionally given antioxidant, and the cellulose derivative and/or the sugars, can be prepared. As a method of removing the solvent, a method of distilling away the solvent is applied. The solvent is preferably distilled away under reduced pressure. Otherwise, a method of removing the solvent according to a spray-drying method may also be adopted.

The above-described solvent for crystallization is added to the solution to prepare a suspension, and the solvent is then removed by filtration, so that a mixture consisting of a solid mixture comprising the components (A) and (B) and optionally given antioxidant, and the cellulose derivative and/or the sugars, can be prepared.

In addition to the aforementioned trehalose, antioxidant, cellulose derivative and sugars, the pharmaceutical composition of the present invention may also comprise other additives that are commonly used in preparation of pharmaceutical product formulations, in a range that does not impair the effects of the present invention. The present pharmaceutical composition may comprise, for example, an excipient, a disintegrator, a binder, a lubricant, a pH adjuster, inorganic salts, and a solvent.

Examples of the excipient include lactose, maltose, mannitol, sucrose, erythritol, sorbitol, fucose, xylitol, fructose, inositol, and starch.

Examples of the disintegrator include carmellose, crospovidone, low-substituted hydroxypropyl cellulose, sodium starch glycolate, carmellose calcium, and croscarmellose sodium.

Examples of the binder include hydroxypropyl cellulose, hypromellose, polyvinyl alcohol, and polyvinyl pyrrolidone.

Examples of the lubricant include magnesium stearate, calcium stearate, sodium stearyl fumarate, talc, and sucrose fatty acid ester.

Examples of the pH adjuster include hydrochloric acid, sulfuric acid, phosphoric acid, citric acid, tartaric acid, malic acid, mesylic acid, tosylic acid, and besylic acid. A buffer, which comprises, as a main ingredient, such an acidic additive, and further, an alkaline metal salt, an alkaline-earth metal salt, or an ammonium salt, may also be used.

Examples of the inorganic salts include calcium chloride, sodium chloride, calcium oxide, and magnesium sulfate.

In general, examples of the solvent include water, a normal saline, a 5% glucose or mannitol aqueous solution, a water-soluble organic solvent (e.g., a single solvent such as glycerol, ethanol, dimethyl sulfoxide, N-methylpyrrolidone, polyethylene glycol, Cremophor, or a mixed solvent thereof), and polyethylene glycols (e.g., polyethylene glycol 300, polyethylene glycol 400, polyethylene glycol 600, polyethylene glycol 4000, etc.).

These additives can be used without any particular limitation, as long as they have purity that is acceptable for the intended use as pharmaceutical product formulations. These additives may be used alone, or may also be used as a mixture of the additives. These additives are optionally used, when the pharmaceutical composition or the pharmaceutical formulation is produced.

<2> Concerning a Method for Producing a Pharmaceutical Composition Comprising Rapamycin or a Derivative Thereof, which Comprises Adding a Solution Containing Rapamycin or a Derivative Thereof to Sugars Having a Critical Relative Humidity at 25° C. of 95% or More The present invention relates to a method for producing a pharmaceutical composition comprising rapamycin or a derivative thereof, which comprises adding a solution containing rapamycin or a derivative thereof to sugars having a critical relative humidity at 25° C. of 95% or more, and a pharmaceutical composition produced by the above-described production method. The details thereof will be described below.

The definitions of the rapamycin and the rapamycin derivative, specific examples thereof, and the like are as described above in the present description.

In the present invention, the solvent used to prepare a solution of rapamycin or a derivative thereof is not particularly limited and any solvent can be applied herein, as long as the rapamycin can be dissolved therein. Examples of the solvent include water, methanol, ethanol, 1-propanol, 2-propanol, 1-butanol, 2-butanol, 2-methyl-1-propanol, 3-methyl-1-butanol, 1-pentanol, ethylene glycol, glycerin, formic acid, acetic acid, acetone, methyl ethyl ketone, methyl isobutyl ketone, anisole, methyl acetate, ethyl acetate, ethyl formate, propyl acetate, isopropyl acetate, n-butyl acetate, isobutyl acetate, acetonitrile, diethyl ether, t-butyl methyl ether, tetrahydrofuran, 1,4-dioxane, thisopropyl ether, pentane, hexane, heptane, N,N-dimethylformamide, N,N-dimethylacetamide, N-methylpyrrolidone, 1,3-dimethyl-2-imidazolidinone, dimethyl sulfoxide, dichloromethane, and chloroform.

These solvents may be used alone, or may also be used as a mixed solvent comprising two or more types of solvents. In the present invention, examples of the solvent used are not limited to the aforementioned solvents, but the aforementioned solvents can be used as applicable preferred solvents.

Taking into consideration the subsequent removal of a solvent, it is preferable to use a solvent having a boiling point of 120° C. or lower, which can be distilled away under mild conditions. Examples of such a preferred solvent include water, methanol, ethanol, 1-propanol, 2-propanol, acetonitrile, acetone, methyl ethyl ketone, ethyl acetate, ethyl acetate, isopropyl acetate, isobutyl acetate, tetrahydrofuran, 1,4-dioxane, pentane, heptane, diethyl ether, and t-butyl methyl ether.

Moreover, as a solvent used in the present invention, a solvent, in which the after-mentioned sugars having a critical relative humidity at 25° C. of 95% or more are insoluble or hardly soluble, is preferable. Accordingly, among the above-described preferred solvents, methanol, ethanol, 1-propanol, 2-propanol, acetone, isopropyl acetate, and ethyl acetate are particularly preferably used. These solvents may be used each alone, or may also be used in combination.

The amount of the solvent used is not particularly limited, as long as the rapamycin or a derivative thereof is completely dissolved therein. Thus, the use amount can be adjusted, as appropriate. It is preferable to prepare a solution containing rapamycin or a derivative thereof in a concentration of 1 to 1000 mg/mL or less, and preferably of 10 to 500 mg/mL.

In addition, upon preparation of the solution, the temperature is increased, as appropriate, so that dissolution of the rapamycin or a derivative thereof may be promoted. The temperature of the solution upon preparation thereof is not particularly limited. Taking into consideration the stability of the rapamycin or a derivative thereof, it is preferable to prepare the solution at a temperature of 0° C. to 80° C.

In the present invention, as a carrier for the pharmaceutical composition, sugars having a critical relative humidity at 25° C. of 95% or more are used. The phrase "a critical relative humidity at 25° C. of 95% or more" means physical properties by which the sugars hardly absorb moisture in a preservation environment in which the relative humidity at 25° C. is 95% or less. The critical relative humidity can be measured, for example, by the method described in the publication, European Journal of Pharmaceutical Sciences 41 (2010) 383-387.

In the present invention, the sugars are not particularly limited and any sugars can be used, as long as they have a critical relative humidity at 25° C. of 95% or more. Sugars having such physical properties can be found in monosaccharides, oligosaccharides, etc., and a person skilled in the art has generally recognized such sugars as sugars having low absorbency.

The sugars having a critical relative humidity at 25° C. of 95% or more are preferably sugar alcohols or disaccharides, and one or more types of sugars selected from the group consisting of mannitol, lactose, trehalose and maltose are preferable. These sugars may be used each alone, or may also be used in combination of two or more types. Lactose is particularly preferably used.

With regard to the addition amount of such sugars having a critical relative humidity at 25° C. of 95% or more used in the present invention, the sugars may be used in an amount of 0.5 parts by mass or more, based on 1 part by mass of the rapamycin or a derivative thereof. The sugars may be used in an amount of preferably 1 part by mass or more, and more preferably 2 parts by mass or more. It is sufficient, if the sugars are used in an amount of 5 parts by mass or more based on 1 part by mass of the rapamycin or a derivative thereof. In the present invention, the upper limit of the use amount of the sugars having a critical relative humidity at 25° C. of 95% or more is not particularly limited, since these sugars are not particularly problematic in terms of safety. Accordingly, the sugars having a critical relative humidity at 25° C. of 95% or more should be used herein in an amount practically usable as a pharmaceutical product.

Taking into consideration the ensuring of the stability of the rapamycin or a derivative thereof and the realistic use amount of a pharmaceutical product additive, the sugars are preferably used in an amount of 0.5 to 100 parts by mass, based on 1 part by mass of the rapamycin or a derivative thereof. The sugars are used in an amount of more preferably 0.5 to 50 parts by mass, even more preferably 1 to 50 parts by mass, and further preferably 2 to 50 parts by mass.

A more preferred aspect of the present invention relates to the use of a solution containing rapamycin or a derivative thereof, which further comprises a stabilizer.

The stabilizer used herein is not particularly limited, as long as it suppresses the oxidation, photolysis, or hydrolysis of rapamycin or a derivative thereof and maintains the stability, when it is added to the rapamycin or a derivative thereof. As such a stabilizer, a known antioxidant or stabilizer exhibiting the effect of stabilizing the rapamycin and a derivative thereof can be used.

Examples of such a stabilizer include nitrous acid, ascorbic acid, sodium ascorbate, ascorhyl stearate, ascorbyl palmitate, sulfurous acid, alpha-thioglycerin, edetic acid, erythorbic acid, cysteine hydrochloride, citric acid, sodium citrate, disodium hydrogen citrate, sodium dihydrogen citrate, dichloroisocyanuric acid, dibutylhydroxytoluene (BHT), thioglycolic acid, thiomalic acid, tocopherol, trehalose, pyrosulfurous acid, butylhydroxyanisole, 1,3-butylene glycol, pentaerythritol tetrakis[3-(3,5-di-t-butyl-4-hydroxyphenyl)propionate]benzotriazole, isopropyl gallate, 2-mercaptobenzimidazole, and lecithin. Examples of the stabilizer used herein are not limited to thereto, but these compounds can be used as stabilizers that are preferably applied to the present invention. The above-described stabilizers may be used each alone, or may also be used in combination.

The stabilizer used herein is more preferably sodium ascorbate, ascorbyl stearate, disodium hydrogen citrate, sodium dihydrogen citrate, dibutylhydroxytoluene (BHT), tocopherol, trehalose, butylhydroxyanisole, isopropyl gallate, or lecithin. The stabilizer used herein is most preferably sodium ascorbate, ascorbyl stearate, disodium hydrogen citrate, dibutylhydroxytoluene (BHT), tocopherol, trehalose, or lecithin.

The above-described stabilizer can be used, as appropriate, in an amount that does not impair the stability of the rapamycin or a derivative thereof. With regard to the addition amount of the above-described stabilizer, the stabilizer is preferably used in an amount of 0.0001 to 10 parts by mass, based on 1 part by mass of the rapamycin or a derivative thereof. The stabilizer is used in an amount of more preferably 0.0005 to 1.0 parts by mass, and further preferably 0.001 to 1.0 part by mass.

It is to be noted that the above-described stabilizer is preferably applied in a state in which it is added to a solution of the rapamycin or a derivative thereof, and is completely dissolved therein.

A more preferred aspect of the present invention relates to the use of a solution containing the rapamycin or a derivative thereof, which further comprises a water-soluble polymer carrier.

The water-soluble polymer carrier is not particularly limited and any water-soluble polymer carrier can be applied herein, as long as it is a water-soluble polymer carrier applicable as an additive to pharmaceutical products. Examples of the water-soluble polymer carrier include a water-soluble synthetic polymer derivative carrier and a water-soluble cellulose derivative carrier.

Examples of the water-soluble synthetic polymer derivative carrier include povidone, macrogol, polyvinyl alcohol, and a methacrylic acid copolymer. These water-soluble synthetic polymer derivative carriers may be used each alone, or may also be used in combination.

The above-described water-soluble polymer carrier used in the present invention is preferably a water-soluble cellulose derivative. The water-soluble cellulose derivative means a water-soluble polymer formed by substituting some hydrogen atoms of the hydroxyl group of cellulose with substituents such as a methyl group, an ethyl group, a propyl group, a hydroxypropyl group, or a carboxymethyl group.

The water-soluble cellulose derivative used in the present invention is preferably a water-soluble cellulose derivative that is acceptable as a pharmaceutical product additive. Specific examples of such a water-soluble cellulose derivative include hydroxypropylmethyl cellulose, hydroxypropyl cellulose, methyl cellulose, ethyl cellulose, hydroxyethyl cellulose, hydroxymethylethyl cellulose, cellacefate, hydroxypropylmethyl cellulose phthalate, hypromellose acetate succinate, hypromellose phthalate, carboxymethyl cellulose, and the alkaline metal salts thereof, such as sodium salt or potassium salts. The water-soluble cellulose derivative is preferably hydroxypropylmethyl cellulose, hydroxypropyl cellulose, methyl cellulose, ethyl cellulose, or hypromellose phthalate. The water-soluble cellulose derivative is most preferably hydroxypropylmethyl cellulose.

With regard to the addition amount of the above-described water-soluble polymer carrier used in the present invention, the water-soluble polymer carrier is preferably used in an amount of 0.1 part by mass or more, based on 1 part by mass of the rapamycin or a derivative thereof. The water-soluble polymer carrier may be more preferably used in an amount of 0.5 parts by mass or more. That is to say, the above-described water-soluble polymer carrier can be used, as appropriate, in an amount that does not impair the stability of the rapamycin or a derivative thereof. With regard to the addition amount of the above-described stabilizer, the water-soluble polymer carrier is preferably used in an amount of 0.1 to 10 parts by mass, based on 1 part by mass of the rapamycin or a derivative thereof. The addition amount of the water-soluble polymer carrier is more preferably 0.1 to 5.0 parts by mass, and further preferably 0.5 to 5.0 parts by mass.

The above-described water-soluble polymer carrier may be used in a state in which it is added to a solution of the rapamycin or a derivative thereof, and is completely dissolved therein, or may also be in a state in which the water-soluble polymer carrier is suspended in the solution. Thus, the water-soluble polymer carrier may be used in any aspects.

In the present invention, the solution containing the rapamycin or a derivative thereof may also comprise other additives that are commonly used in preparation of pharmaceutical product formulations, in a range that does not impair the effects of the present invention. For instance, the solution containing the rapamycin or a derivative thereof may comprise a pH adjuster, inorganic salts, etc.

Specific examples of the pH adjuster and the inorganic salts used herein are the same as those described above in the present description.

When other additives are used, the additives are preferably used in an amount of 0.01 to 10 parts by mass, based on 1 part by mass of the rapamycin or a derivative thereof.

The above-described other additives may be used in a state in which they are added to a solution of the rapamycin or a derivative thereof, and are completely dissolved therein, or may also be in a state in which the additives are suspended in the solution. Thus, other additives may be used in any aspects.

The pharmaceutical composition of the present invention is produced by adding the above-described solution containing the rapamycin or a derivative thereof, etc., to solid-state sugars having a critical relative humidity at 25° C. of 95% or more, and then mixing them with each other.

The solid-state sugars having a critical relative humidity at 25° C. of 95% or more are preferably the sugars alone. However, the sugars may also comprise other additives that are commonly used in preparation of pharmaceutical product formulations, in a range that does not impair the effects of the present invention. That is, the present invention may include, as a feature thereof, addition of a solution containing rapamycin or a derivative thereof to a solid carrier containing sugars having a critical relative humidity at 25° C. of 95% or more.

Examples other additives that may be applied herein include an excipient, a disintegrator, a binder, a lubricant, a pH adjuster, and inorganic salts.

Specific examples of such an excipient, a disintegrator, a binder, a lubricant, a pH adjuster, and inorganic salts are the same as those described above in the present description.

These additives can be used without any particular limitation, as long as they have purity that is acceptable for the intended use as pharmaceutical product formulations. These additives may be used alone, or may also be used as a mixture of the additives. These additives are optionally used, when the pharmaceutical composition or the pharmaceutical formulation is produced.

The method of adding the above-described solution containing rapamycin or a derivative thereof, etc. to the above-described solid-state sugars is not particularly limited. An addition method of homogeneously mixing the solution containing rapamycin, etc. with the sugars is preferably applied. As such, a method of adding the solution dropwise to the sugars is preferable. A method of adding the solution dropwise to the sugars in a spay form is more preferable. A method of adding the solution dropwise to the sugars, while mixing the sugars, is further preferable.

Regarding the pharmaceutical composition of the present invention, it is preferable to add the above-described solution containing rapamycin or a derivative thereof, etc. to the above-described sugars that are in a solid state, and then, to remove the solvent from the mixed solution. For example, the solvent can be removed from the above-described solution by heating it. Upon such removal, the conditions are preferably set to be reduced pressure conditions, since the solvent can be removed under mild temperature conditions. Moreover, a solid mixture can also be obtained by ventilation drying, in which inert gas such as air or nitrogen is supplied into a dryer.

The pharmaceutical composition of the present invention can suppress oxidation or decomposition of the rapamycin or a derivative thereof comprised as an active ingredient, and can prevent a reduction in the content of the active ingredient caused by such oxidation or decomposition. Thus, in the present invention, a pharmaceutical composition having excellent preservation stability can be produced. In the present invention, the preservation stability can be evaluated by a test method regarding physicochemical stability in the development of pharmaceutical products. In the present invention, the preservation stability is considered to be a physical property, by which the content of the rapamycin or a derivative thereof is at least 80% of the initial value, when the pharmaceutical composition has been preserved under light-shielded conditions, at 60° C., in a storage box that has been adjusted to a relative humidity of approximately 49% with a saturated cobalt chloride aqueous solution, for 14 days, for example, according to an accelerated test.

Using the pharmaceutical composition of the present invention produced by the aforementioned method, a pharmaceutical formulation can be produced. Specifically, additives, which are commonly used to prepare pharmaceutical product formulations, are combined with the pharmaceutical composition of the present invention, so that a pharmaceutical formulation can be produced. As other additives, for example, an excipient, a disintegrator, a binder, a lubricant, a pH adjuster, inorganic salts, a solvent, etc. may be applied.

Specific examples of such an excipient, a disintegrator, a binder, a lubricant, a pH adjuster, inorganic salts, and a solvent are the same as those described above in the present description.

These additives can be used without any particular limitation, as long as they have purity that is acceptable for the intended use as pharmaceutical product formulations. These additives may be used alone, or may also be used as a mixture of the additives. These additives are optionally used, when the pharmaceutical composition or the pharmaceutical formulation is produced.

<3> Concerning the Dosage Form, Intended Use and Usage of the Pharmaceutical Composition of the Present Invention The pharmaceutical composition of the present invention described in the above <1> and <2> can be produced in the form of a pharmaceutical product comprising the pharmaceutical composition.

Examples of the dosage form of this pharmaceutical product include: internal use agents, such as a tablet, a dispersible tablet, a chewable tablet, an effervescent tablet, a troche, a drop agent, a hard capsule, a soft capsule, a granule, a powder agent, a pill, dry syrup, infusions and/or decoctions, an electuary, syrup, a drink agent, a suspension, an orally disintegrating tablet, and a jelly agent; and external use agents, such as a suppository, a poultice, a plaster, an ointment, a cream agent, a mousse agent solution, a liquid agent, eye drops, an aerosol agent, and a spray agent. The dosage forms are not limited thereto, but these are applicable preferred dosage forms.

In a case where the pharmaceutical composition of the present invention is used in the form of an injection, examples of such an injection include an aqueous injection, a non-aqueous injection, a suspension injection, an emulsion injection, and also, as dosage forms of being dissolved or suspended at the time of use, an intradermal injection, a subcutaneous injection, an intramuscular injection, an intravenous injection, a central intravenous injection, an intra-arterial injection, and an intrathecal injection. Examples of the injection used herein are not limited thereto, but these injections can be used as applicable preferred dosage forms and administration routes.

The pharmaceutical product, in which the pharmaceutical composition of the present invention is used, can be applied to the treatment of disease. Examples of the disease, to which the pharmaceutical product can be applied include: transplant rejection in transplantation of heart, lung, combined heart-lung, liver, kidney, pancreas, skin, or cornea; autoimmune diseases, and inflammatory diseases, such as arthritis, rheumatic disease, systemic lupus erythematosus, multi polychondritis, crusts disease, Wegener's granulomatosis, dermatomyositis, chronic active hepatitis, myasthenia gravis, psoriasis, Steven-Johnson syndrome, idiopathic sprue, autoimmune inflammatory bowel disease, endocrine ophthalmopathy, Graves disease, nodule colitis, multiple sclerosis, primary biliary hepatitis, juvenile diabetes (type 1 diabetes), uveitis, keratoconjunctivitis sicca, vernal keratoconjunctivitis, interstitial lung fibrosis, psoriatic arthritis, glomerulonephritis, and juvenile dermatomyositis; asthma; and cancers and hyperproliferative diseases, such as breast cancer, renal cancer, neuroendocrine tumor, lymphoid proliferative disease, B cell lymphatic cancer, tuberous sclerosis, and proliferative skin disease. Examples of the disease are not limited thereto, but these diseases can be considered to be applicable preferred diseases.

The applied dose of the pharmaceutical product comprising the pharmaceutical composition of the present invention can be naturally changed, depending on the sex, age, physiological conditions, pathologic conditions of a patient, etc. For example, the rapamycin or a derivative thereof is administered to an adult patient at a daily dose of 0.01 to 100 mg/m$^2$ (body surface area). The dose of the pharmaceutical product is not limited thereto, but this dose can be used as an applicable preferred dose.

EXAMPLES

Hereinafter, the present invention will be more specifically described in the following examples. However, these examples are not intended to limit the scope of the present invention.

It is to be noted that, in the analysis using liquid chromatography (HPLC) in the present test examples, the measurement was carried out under the following conditions.
Measurement column: Zorbax Eclipse XDB-C18, Rapid resolution HT, 100 mm×4.6 mm, 1.8 μm
Detector: ultraviolet absorption spectrophotometer (measurement wavelength: 278 nm)
Column temperature: 45° C.
Mobile phase A: 0.1% formic acid; mobile phase B: methanol/acetonitrile=50/50
Concentration gradient of mobile phase:

TABLE 1

| Time after injection (min) | Mobile phase A (vol %) | Mobile phase B (vol %) |
|---|---|---|
| 0-5 | 46 | 64 |
| 5-17 | 46 → 25 | 64 → 75 |
| 17-22 | 25 → 10 | 75 → 90 |
| 22-24 | 10 | 90 |
| 24-25 | 10 → 46 | 90 → 64 |
| 25-28 | 46 | 64 |

Flow rate: 1.5 mL/min
Injection amount: 10 μL

Example A1

70 mg of Everolimus was weighed into a test tube, and 350 μL of EtOH was then added thereto. The mixture was irradiated with ultrasonic wave for 10 minutes, and thereafter, dissolution of everolimus was confirmed. To the obtained solution, 100 μL of a trehalose dihydrate (manufactured by Wako Pure Chemical Industries, Ltd.) aqueous solution (829 mg/mL) was added. Thereafter, 630 mg of anhydrous lactose (Super Tab (registered trademark) 21 AN, manufactured by DFE Pharma) and 70 mg of hypromellose (TC-5 E Type, manufactured by Shin-Etsu Chemical Co., Ltd.) were weighed into a mortar, and these substances were then stirred using a pestle to obtain a mixture. Thereafter, the above-obtained mixed solution was added dropwise to this mixture, using a Pasteur pipette, and the thus obtained mixture was then stirred using a pestle. The obtained powders were transferred into an egg-plant shaped flask, and were then dried using an evaporator under reduced pressure for 3 hours, so as to produce the pharmaceutical composition comprising everolimus of Example A1.

Comparative Example A1

70 mg of Everolimus was weighed into a test tube, and 200 μL of EtOH was then added thereto. The mixture was irradiated with ultrasonic wave for 10 minutes, and thereafter, dissolution of everolimus was confirmed. After that, 630 mg of anhydrous lactose (Super Tab (registered trademark) 21 AN, manufactured by DFE Pharma) and 70 mg of hypromellose (TC-5 E Type, manufactured by Shin-Etsu Chemical Co., Ltd.) were weighed into a mortar, and these substances were then stirred using a pestle to obtain a mixture. Thereafter, the above-obtained solution was added dropwise to this mixture, using a Pasteur pipette, and the thus obtained mixture was then stirred using a pestle. The obtained powders were transferred into an egg-plant shaped flask, and were then dried using an evaporator under reduced pressure for 3 hours, so as to produce the pharmaceutical composition comprising everolimus of Comparative Example A1.

Comparative Example A2

70 mg of Everolimus was weighed into a test tube, and 100 μL of a dihydroxybutyltoluene (BHT, manufactured by MERCK) EtOH solution (14 mg/mL) was then added thereto. The mixture was irradiated with ultrasonic wave for 10 minutes, and thereafter, dissolution of everolimus was confirmed, After that, 100 μL of EtOH was added to the mixed solution to dilute it. Thereafter, 630 mg of anhydrous lactose (Super Tab (registered trademark) 21 AN, manufactured by DFE Pharma) and 70 mg of hypromellose (TC-5 E Type, manufactured by Shin-Etsu Chemical Co., Ltd.) were weighed into a mortar, and these substances were then stirred using a pestle to obtain a mixture. Thereafter, the above-obtained solution was added dropwise to this mixture, using a Pasteur pipette, and the thus obtained mixture was then stirred using a pestle. The obtained powders were transferred into an egg-plant shaped flask, and were then dried using an evaporator under reduced pressure for 3 hours, so as to produce the pharmaceutical composition comprising everolimus of Comparative Example A2.

Comparative Example A3

70 mg of Everolimus was weighed into a test tube, and 100 μL of a DL-α-tocopherol (Riken E Oil 1000, manufactured by RIKEN VITAMIN CO., LTD.) EtOH solution (14 mg/mL) was then added thereto. The mixture was irradiated with ultrasonic wave for 10 minutes, and thereafter, dissolution of everolimus was confirmed. After that, 100 μL of EtOH was added to the mixed solution to dilute it. Thereafter, 630 mg of anhydrous lactose (Super Tab (registered trademark) 21 AN, manufactured by DFE Pharma) and 70 mg of hypromellose (TC-5 E Type, manufactured by Shin-Etsu Chemical Co., Ltd.) were weighed into a mortar, and these substances were then stirred using a pestle to obtain a mixture. Thereafter, the above-obtained solution was added dropwise to this mixture, using a Pasteur pipette, and the thus obtained mixture was then stirred using a pestle. The obtained powders were transferred into an egg-plant shaped flask, and were then dried using an evaporator under reduced pressure for 3 hours, so as to produce the pharmaceutical composition comprising everolimus of Comparative Example A3.

Test Example A1

The pharmaceutical compositions of Example A1 and Comparative Examples A1 to A3 (approximately 600 mg each) were each collected into a brown sample bottle, and were then preserved under light-shielded conditions at 60° C., in a desiccator, the humidity of which had been adjusted with a saturated cobalt chloride aqueous solution, while the bottle was uncapped.

The residual amounts of everolimus 7 days and 14 clays after initiation of the preservation were measured by liquid chromatography (HPLC), and the residual percentages of everolimus at individual time points were then calculated. It is to be noted that the residual percentage was calculated according to the following formula. The results are shown in Table 2.

Residual percentage (%) of everolimus=(peak area of everolimus measured by HPLC at each time point/weighed value of powders)/(peak area of everolimus measured by HPLC before preservation (initial)/weighed value of powders)×100

TABLE 2

| | | Residual percentage (%) of everolimus | |
|---|---|---|---|
| | Additive | Value on Day 7 | Value on Day 14 |
| Example A1 | Trehalose | 93 | 75 |
| Comparative Example A1 | — | 72 | 28 |
| Comparative Example A2 | BHT | 95 | 60 |
| Comparative Example A3 | Tocopherol | 70 | 35 |

A decomposition reaction such as oxidation progresses in a pharmaceutical composition comprising everolimus at 60° C. under humidified conditions, and as a result, the content of everolimus is reduced. In Test Example A1, in the case of the pharmaceutical composition comprising everolimus according to Comparative Example A2, which had been produced only with anhydrous lactose and hypromellose (hydroxypropylniethyl cellulose), a rapid reduction in the content of everolimus was observed. In contrast, in the case of the pharmaceutical composition according to Example A1, to which trehalose had been added, the content of everolimus was high even 14 days after initiation of the preservation, and thus, it was found that this pharmaceutical composition was stabilized.

BHT used in Comparative Example A2 is an antioxidant, which suppresses oxidation of everolimus by oxidation of the BHT itself. In the pharmaceutical composition according to Comparative Example A2 comprising BHT, significant decomposition of everolimus was observed from 7 days after initiation of the preservation, and thus, consumption of the BHT was assumed. It became clear that the pharmaceutical composition of Example A1 according to the present invention has excellent performance regarding continuation of stabilization effects for a long period of time, in comparison to the comparative examples.

Example A2

50 mg of Everolimus was weighed into a test tube, and 300 μL of EtOH was then added thereto. The mixture was irradiated with ultrasonic wave for 10 minutes, and thereafter, dissolution of everolimus was confirmed. To the obtained solution, 133.34 μL of a trehalose dihydrate (manufactured by Wako Pure Chemical Industries, Ltd.) aqueous solution (592.25 mg/mL) and 10 μL of a sodium ascorbate (manufactured by FUSO CHEMICAL CO., LTD.) aqueous solution (100 mg/mL) were added. Thereafter, 450 mg of anhydrous lactose (Super Tab (registered trademark) 21 AN, manufactured by DFE Pharma) and 50 mg of hypromellose (TC-5 E Type, manufactured by Shin-Etsu Chemical Co., Ltd.) were weighed into a mortar, and these substances were then stirred using a pestle to obtain a mixture. Thereafter, the above-obtained mixed solution was added dropwise to this mixture, using a Pasteur pipette, and the thus obtained mixture was then stirred using a pestle. The obtained powders were transferred into an egg-plant shaped flask, and were, then dried using an evaporator under reduced pressure for 3 hours, so as to produce the pharmaceutical composition comprising everolimus of Example A2.

Example A3

50 mg of Everolimus was weighed into a test tube, and 100 μL of ascorbic acid (manufactured by FUSO CHEMICAL CO., LTD.) EtOH solution (10 mg/mL) was then added thereto. The mixture was irradiated with ultrasonic wave for 10 minutes, and thereafter, dissolution of everolimus was confirmed. To the mixed solution, 200 μL of EtOH was added, so as to dilute the solution, and then, 133.34 μL of a trehalose dihydrate (manufactured by Wako Pure Chemical Industries, Ltd.) aqueous solution (592.25 mg/mL) was added thereto. Thereafter, 450 mg of anhydrous lactose (Super Tab (registered trademark) 21 AN, manufactured by DFE Pharma) and 50 mg of hypromellose (TC-5 E Type, manufactured by Shin-Etsu Chemical Co., Ltd.) were weighed into a mortar, and these substances were then stirred using a pestle to obtain a mixture. Thereafter, the above-obtained mixed solution was added dropwise to this mixture, using a Pasteur pipette, and the thus obtained mixture was then stirred using a pestle. The obtained powders were transferred into an egg-plant shaped flask, and were then dried using an evaporator under reduced pressure for 3 hours, so as to produce the pharmaceutical composition comprising everolimus of Example A3.

Example A4

50 mg of Everolimus was weighed into a test tube, and 300 μL of EtOH was then added thereto. The mixture was irradiated with ultrasonic wave for 10 minutes, and thereafter, dissolution of everolimus was confirmed. To the obtained solution, 200 μL of a trehalose dihydrate (manufactured by Wako Pure Chemical Industries, Ltd.) aqueous solution (592.25 mg/mL) was added. Thereafter, 450 mg of anhydrous lactose (Super Tab (registered trademark) 21 AN, manufactured by DFE Pharma) and 50 mg of hypromellose (TC-5 E Type, manufactured by Shin-Etsu Chemical Co., Ltd.) were weighed into a mortar, and these substances were then stirred using a pestle to obtain a mixture. Thereafter, the above-obtained mixed solution was added dropwise to this mixture, using a Pasteur pipette, and the thus obtained mixture was then stirred using a pestle. The obtained powders were transferred into an egg-plant shaped flask, and were then dried using an evaporator under reduced pressure for 3 hours, so as to produce the pharmaceutical composition comprising everolimus of Example A4.

Comparative Example A4

50 mg of Everolimus was weighed into a test tube, and 100 μL of a dihydroxybutyltoluene (BHT, manufactured by MERCK) EtOH solution (10 mg/mL) was then added thereto. The mixture was irradiated with ultrasonic wave for 10 minutes, and thereafter, dissolution of everolimus was confirmed. To the mixed solution, 100 μL of EtOH was added, so as to dilute the solution. Thereafter, 450 mg of anhydrous lactose (Super Tab (registered trademark) 21 AN, manufactured by DFE Pharma) and 50 mg of hypromellose (TC-5 E Type, manufactured by Shin-Etsu Chemical Co., Ltd.) were weighed into a mortar, and these substances were then stirred using a pestle to obtain a mixture. Thereafter, the above-obtained solution was added dropwise to this mixture, using a Pasteur pipette, and the thus obtained mixture was then stirred using a pestle. The obtained powders were transferred into an egg-plant shaped flask, and were then dried using an evaporator under reduced pressure for 3 hours, so as to produce the pharmaceutical composition comprising everolimus of Comparative Example A4.

Example A5

50 mg of Everolimus was weighed into a test tube, and 300 μL of EtOH was then added thereto. The mixture was irradiated with ultrasonic wave for 10 minutes, and thereafter, dissolution of everolimus was confirmed. To the obtained solution, 200 μL of a trehalose dihydrate (manufactured by Wako Pure Chemical Industries, Ltd.) aqueous solution (592.25 mg/mL), 10 μL of a sodium ascorbate (manufactured by FUSO CHEMICAL CO., LTD.) aqueous solution (100 mg/mL), and 10 μL of a disodium hydrogen citrate (Wako Pure Chemical Industries, Ltd.) aqueous solution (100 mg/mL) were added. Thereafter, 450 mg of anhydrous lactose (Super Tab (registered trademark) 21 AN, manufactured by DFE Pharma) and 50 mg of hypromellose (TC-5 E Type, manufactured by Shin-Etsu Chemical Co., Ltd.) were weighed into a mortar, and these substances were then stirred using a pestle to obtain a mixture. Thereafter, the above-obtained mixed solution was added dropwise to this mixture, using a Pasteur pipette, and the thus obtained mixture was then stirred using a pestle. The obtained powders were transferred into an egg-plant shaped flask, and were then dried using an evaporator under reduced pressure for 3 hours, so as to produce the pharmaceutical composition comprising everolimus of Example A5.

Comparative Example A5

50 mg of Everolimus was weighed into a test tube, and 100 μL of a dihydroxybutyltoluene (BHT, manufactured by MERCK) EtOH solution (10 mg/mL) was then added thereto. The mixture was irradiated with ultrasonic wave for 10 minutes, and thereafter, dissolution of everolimus was confirmed. To the mixed solution, 100 μL of EtOH was added, so as to dilute the solution. Thereafter, 450 mg of anhydrous lactose (Super Tab (registered trademark) 21 AN, manufactured by DFE Pharma) and 50 mg of hypromellose (TC-5 E Type, manufactured by Shin-Etsu Chemical Co., Ltd.) were weighed into a mortar, and these substances were then stirred using a pestle to obtain a mixture. Thereafter, the above-obtained solution was added dropwise to this mixture, using a Pasteur pipette, and the thus obtained mixture was then stirred using a pestle. The obtained powders were transferred into an egg-plant shaped flask, and were then dried using an evaporator under reduced pressure for 3 hours, so as to produce the pharmaceutical composition comprising everolimus of Comparative Example A5.

Test Example A2

The pharmaceutical compositions obtained by the methods of Examples A2 to A5 and Comparative Examples A4 and A5 (approximately 500 mg each) were each collected into a brown sample bottle, and were then preserved under light-shielded conditions at 60° C., in a desiccator, the humidity of which had been adjusted with a saturated cobalt chloride aqueous solution, while the bottle was uncapped. Moreover, the pharmaceutical compositions obtained by the methods of Example A5 and Comparative Example A5 (approximately 500 mg each) were each collected into a brown sample bottle, and were then preserved under light-shielded conditions at 60° C., in a desiccator, the humidity of which had been adjusted with a saturated cobalt chloride aqueous solution, while the bottle was uncapped.

The residual amounts of everolimus 7 or 10 days, and 17 days after initiation of the preservation were measured by liquid chromatography (HPLC), and the residual percentages of everolimus at individual time points were then calculated. It is to be noted that the residual percentage was calculated according to the following formula. The results are summarized in Table 3 and Table 4. Residual percentage (%) of everolimus=(peak area of everolimus measured by HPLC at each time point/weighed value of powders)/(peak area of everolimus measured by HPLC before preservation (initial)/weighed value of powders)×100.

TABLE 3

| | | Residual percentage (%) of Everolimus | |
|---|---|---|---|
| | Additive | Value on Day 7 | Value on Day 17 |
| Example A2 | Trehalose + Na ascorbate | 97 | 94 |

TABLE 3-continued

| | Additive | Residual percentage (%) of Everolimus | |
|---|---|---|---|
| | | Value on Day 7 | Value on Day 17 |
| Example A3 | Trehalose + ascorbic acid | 96 | 92 |
| Example A4 | Trehalose | 98 | 92 |
| Comparative Example A4 | BHT | 96 | 89 |

TABLE 4

| | Additive | Residual percentage (%) of Everolimus | |
|---|---|---|---|
| | | Value on Day 10 | Value on Day 17 |
| Example A5 | Trehalose + Na ascorbate + 2Na citrate | 95 | 94 |
| Comparative Example A5 | BHT | 94 | 91 |

As a result, it was found that the pharmaceutical compositions of Example A2 to A5 exhibited stabilization effects that were equivalent to or greater than those of BHT used as an antioxidant in everolimus formulations. It has been reported that BHT exhibits carcinogenicity or reproduction toxicity, and thus, this is a substance, the use amount of which is limited. It has been known that trehalose, ascorbic acid and citric acid, used in Example A2 to A5, are highly safe additives that have been broadly used as pharmaceutical product additives or food product additives. Accordingly, the present invention can provide a pharmaceutical formulation, which avoids the use of a synthetic antioxidant that is problematic in terms of safety, and exhibits the effect of stabilizing rapamycin or a derivative thereof that is equivalent to or greater than that of the synthetic antioxidant.

Example B1

150 mg of Everolimus was weighed into a test tube, and 10 μL of a dibutylhydroxytoluene (BHT, manufactured by MERCK) anhydrous ethanol solution (30 mg/mL) and 750 μL of anhydrous ethanol were then added thereto. The mixture was irradiated with ultrasonic wave for 5 minutes, and thereafter, dissolution of everolimus was confirmed. To the mixed solution, 150 mg of hypromellose (TC-5 E Type, manufactured by Shin-Etsu Chemical Co., Ltd.) was added, and the thus obtained mixture was then irradiated with ultrasonic wave for 5 minutes. Thereafter, 1350 mg of anhydrous lactose (Super Tab (registered trademark) 21 AN, manufactured by DFE Pharma) was weighed into a mortar, and the above obtained mixed solution was then added dropwise thereto, using a Pasteur pipette. The thus obtained mixture was then stirred using a pestle. The obtained powders were transferred into an egg-plant shaped flask, and were then dried using an evaporator under reduced pressure for 3 hours, so as to produce the pharmaceutical composition of Example B1. It is to be noted that the critical relative humidity at 25° C. of lactose is 95% or more.

Comparative Example B1

150 mg of Everolimus was weighed into a test tube, and 10 μL of a dibutylhydroxytoluene (BHT, manufactured by MERCK) anhydrous ethanol solution (30 mg/mL) and 75 mL of anhydrous ethanol were then added thereto. Thereafter, using a homogenizer (ULTRA-TURRAX (registered trademark) T25 digital, manufactured by IKA), the mixture was stirred at 10,000 rpm for 1 minute, and dissolution of everolimus was then confirmed. To the mixed solution, 1350 mg of hypromellose (TC-5 E Type, manufactured by Shin-Etsu Chemical Co., Ltd.) and 150 mg of anhydrous lactose (Super Tab (registered trademark) 21 AN, manufactured by DFE Pharma) were added, and using a homogenizer (ULTRA-TURRAX (registered trademark) T25 digital, manufactured by IKA), the obtained mixture was further stirred at 10,000 rpm for 60 minutes. Thereafter, the mixed solution was spray-dried using a spray dryer (Mini Spray Dryer B-290, manufactured by BUCHI), so as to produce the pharmaceutical composition of Comparative Example B1.

Comparative Example B2

150 mg of Everolimus was weighed into a test tube, and 10 μL of a dibutylhydroxytoluene (BHT, manufactured by MERCK) anhydrous ethanol solution (30 mg/mL) and 750 μL of anhydrous ethanol were then added thereto. Thereafter, the mixture was irradiated with ultrasonic wave for 5 minutes, and dissolution of everolimus was then confirmed. After that, 1500 mg of hypromellose (TC-5 E Type, manufactured by Shin-Etsu Chemical Co., Ltd.) was weighed into a mortar, and then, using a Pasteur pipette, the above-obtained mixed solution was added dropwise thereto. The thus obtained mixture was stirred using a pestle. The obtained powders were transferred into an egg-plant shaped flask, and were then dried using an evaporator under reduced pressure for 3 hours, so as to produce the pharmaceutical composition of Comparative Example B2.

Comparative Example B3

75 mg of Hypromellose (TC-5 E Type, manufactured by Shin-Etsu Chemical Co., Ltd.) was weighed into a test tube, and 300 μL of water was then added thereto, so that the hypromellose was dissolved in the water. Thereafter, 150 mg of everolimus and 1425 mg of anhydrous lactose (Super Tab (registered trademark) 21 AN, manufactured by DFE Pharma) were weighed into a mortar, and these substances were then stirred using a pestle to obtain a mixture. Thereafter, the above-obtained solution was added dropwise to this mixture, using a Pasteur pipette, and the thus obtained mixture was then stirred using a pestle. Moreover, 10 μL of a dibutylhydroxytoluene (BHT, manufactured by MERCK) anhydrous ethanol solution (30 mg/mL) was added to the reaction mixture, and the thus obtained mixture was then stirred using a pestle. The obtained powders were transferred into an egg-plant shaped flask, and were then dried using an evaporator under reduced pressure for 3 hours, so as to produce the pharmaceutical composition of Comparative Example B3.

Comparative Example B4

150 mg of Everolimus, 150 mg of anhydrous lactose (Super Tab (registered trademark) 21 AN, manufactured by DFE Pharma), 1350 mg of hypromellose (TC-5 E Type, manufactured by Shin-Etsu Chemical Co., Ltd.) and 0.3 mg of dibutylhydroxytoluene (BHT, manufactured by MERCK) were weighed into a mortar, and the obtained mixture was then stirred using a pestle. The mixed powders were molded using a single tablet-making machine, and the molded product was then crushed, so as to produce the pharmaceutical composition of Comparative Example B4.

Test Example B1

The pharmaceutical compositions obtained by the methods of Example B1 and Comparative Examples B1 to B4 (approximately 1 g each) and the active pharmaceutical ingredient of everolimus (100 mg) were each collected in a brown sample bottle, and were then preserved under light-shielded conditions at 60° C., in a desiccator, the humidity of which had been adjusted with a saturated cobalt chloride aqueous solution (relative humidity: approximately 49%), while the bottle was uncapped.

The residual amounts of everolimus 10 days and 14 days after initiation of the preservation test were measured by liquid chromatography (HPLC), and the residual percentages of everolimus at individual time points were then calculated. It is to be noted that the residual percentage was calculated according to the following formula. The results are shown in Table 5.

Residual percentage (%) of everolimus=(peak area of everolimus measured by HPLC at each time point/weighed value of powders)/(peak area of everolimus measured by HPLC before preservation (initial)/weighed value of powders)×100

TABLE 5

| | Residual percentage (%) of everolimus | |
| --- | --- | --- |
| | Value on Day 10 | Value on Day 14 |
| Example B1 | 93 | 89 |
| Comparative Example B1 | 70 | 56 |
| Comparative Example B2 | 80 | 71 |
| Comparative Example B3 | 39 | 28 |
| Comparative Example B4 | 48 | 39 |
| Active pharmaceutical ingredient of everolimus | 5 | 2 |

The active pharmaceutical ingredient of everolimus has physical properties by which a decomposition reaction such as oxidation rapidly progresses when it is preserved under light-shielded conditions at 60° C. in a saturated cobalt chloride aqueous solution (relative humidity: approximately 49%). Under such circumstances, the currently commercially available everolimus formulations (Afinitor (registered trademark) tablets and Certican (registered trademark) tablets) are produced in the form of pharmaceutical compositions comprising hypromellose, lactose and dibutylhydroxytoluene (BHT)) as well as everolimus.

Comparative Example B1 relates to a composition produced by imitating the pharmaceutical composition disclosed in Patent Literature 1 (JP Patent Publication (Kohyo) No. 11-509223 A (1999)). In addition, Comparative Example B2 relates to a pharmaceutical composition produced by considering the stability of everolimus disclosed in Patent Literature 4 (International Publication. WO 2013/022201).

It has been shown that the pharmaceutical composition of Example B1 suppresses oxidation or the like of everolimus and exhibits high stability, in comparison to known pharmaceutical compositions. This shows that the stability of everolimus is greatly influenced not only by the formulation of additives, but also by the production method thereof. That is to say, it has been elucidated that a pharmaceutical composition produced by a method of adding an everolimus solution to lactose improves the stability of the everolimus.

That is, it has been demonstrated that the pharmaceutical composition of Example B1 according to the present invention has stability, by which when the pharmaceutical composition has been preserved under light-shielded conditions at 60° C. at a relative humidity of approximately 49% that has been adjusted with a saturated cobalt chloride solution, the content of everolimus used as an active ingredient has been 80% or more 14 days after initiation of the preservation.

Therefore, the pharmaceutical composition of Example B1 according to the present invention is ensured to comprise an active ingredient capable of expressing medicinal effects and can prevent the expression of side effects that would be caused by decomposition products. Hence, it has been demonstrated that the present invention can provide a pharmaceutical formulation, in which the stability of an active ingredient such as everolimus is high and safety is also high.

Example B2

30 mg of Everolimus was weighed into a test tube, and 10 μL of a dibutylhydroxytoluene (BHT, manufactured by MERCK) anhydrous ethanol solution (6 mg/mL) and 120 μL of anhydrous ethanol were then added thereto. The mixture was irradiated with ultrasonic wave for 5 minutes, and thereafter, dissolution of everolimus was confirmed. After that, 30 mg of hyproniellose (TC-5 E Type, manufactured by Shin-Etsu. Chemical Co., Ltd.) was added to the mixed solution, and the thus obtained mixture was then irradiated with ultrasonic wave for 5 minutes. Thereafter, 270 mg of trehalose (manufactured by Hayashihara Co., Ltd.) was weighed into a mortar, and then, using a Pasteur pipette, the above-obtained mixed solution was added dropwise thereto. The thus obtained mixture was stirred using a pestle. The obtained powders were transferred into an egg-plant shaped flask, and were then dried using an evaporator under reduced pressure for 3 hours, so as to produce the pharmaceutical composition of Example B2. It is to be noted that the critical relative humidity at 25° C. of trehalose is 95% or more.

Example B3

30 mg of Everolimus was weighed into a test tube, and 10 μL of a dibutylhydroxytoluene (BHT, manufactured by MERCK) anhydrous ethanol solution (6 mg/mL) and 120 μL of anhydrous ethanol were then added thereto. The mixture was irradiated with ultrasonic wave for 5 minutes, and thereafter, dissolution of everolimus was confirmed. After that, 30 mg of hypromellose (TC-5 E Type, manufactured by Shin-Etsu Chemical Co., Ltd.) was added to the mixed solution, and the thus obtained mixture was then irradiated with ultrasonic wave for 5 minutes. Thereafter, 270 mg of D-mannitol (manufactured by Roquette Pharma) was weighed into a mortar, and then, using a Pasteur pipette, the above-obtained mixed solution was added dropwise thereto. The thus obtained mixture was stirred using a pestle. The obtained powders were transferred into an egg-plant shaped flask, and were then dried using an evaporator under reduced pressure for 3 hours, so as to produce the pharmaceutical composition of Example B3. It is to be noted that the critical relative humidity at 25° C. of mannitol is 95% or more.

Comparative Example B5

30 mg of Everolimus was weighed into a test tube, and 10 μL of a dibutylhydroxytoluene (BHT, manufactured by MERCK) anhydrous ethanol solution (6 mg/mL) and 120 μL of anhydrous ethanol were then added thereto. The mixture was irradiated with ultrasonic wave for 5 minutes, and thereafter, dissolution of everolimus was confirmed. After that, to the mixed solution, 30 mg of hypromellose (TC-5 E Type, manufactured by Shin-Etsu Chemical Co., Ltd.) was added, and the obtained mixture was then irradiated with ultrasonic wave for 5 minutes. Thereafter, 270 mg of sorbitol (manufactured by MERCK Japan) was weighed into a mortar, and then, using a Pasteur pipette, the above-obtained mixed solution was added dropwise thereto. The thus obtained mixture was stirred using a pestle. The obtained powders were transferred into an egg-plant shaped flask, and were then dried using an evaporator under reduced pressure for 3 hours, so as to produce the pharmaceutical composition of Comparative Example B5. It is to be noted that the critical relative humidity at 25° C. of sorbitol is approximately 70%.

Comparative Example B6

30 mg of Everolimus was weighed into a test tube, and 10 μL of a dibutylhydroxytoluene (BHT, manufactured by MERCK) anhydrous ethanol solution (6 mg/mL) and 120 μL of anhydrous ethanol were then added thereto. The mixture was irradiated with ultrasonic wave for 5 minutes, and thereafter, dissolution of everolimus was confirmed. After that, to the mixed solution, 30 mg of hypromellose (TC-5 E Type, manufactured by Shin-Etsu Chemical Co., Ltd.) was added, and the obtained mixture was then irradiated with ultrasonic wave for 5 minutes. Thereafter, 270 mg of glucose (manufactured by San-ei Sucrochemical Co., Ltd.) was weighed into a mortar, and then, using a Pasteur pipette, the above-obtained mixed solution was added dropwise thereto. The thus obtained mixture was stirred using a pestle. The obtained powders were transferred into an egg-plant shaped flask, and were then dried using an evaporator under reduced pressure for 3 hours, so as to produce the pharmaceutical composition of Comparative Example B6. It is to be noted that the critical relative humidity at 25° C. of glucose is approximately 90%.

Comparative Example B7

30 mg of Everolimus was weighed into a test tube, and 10 μL of a dibutylhydroxytoluene (BHT, manufactured by MERCK) anhydrous ethanol solution (6 mg/mL) and 120 μL of anhydrous ethanol were then added thereto. The mixture was irradiated with ultrasonic wave for 5 minutes, and thereafter, dissolution of everolimus was confirmed. Thereafter, 300 mg of hypromellose (TC-5 E Type, manufactured by Shin-Etsu Chemical Co., Ltd.) was weighed into a mortar, and then, using a Pasteur pipette, the above-obtained mixed solution was added dropwise thereto. The thus obtained mixture was stirred using a pestle. The obtained powders were transferred into an egg-plant shaped flask, and were then dried using an evaporator under reduced pressure for 3 hours, so as to produce the pharmaceutical composition of Comparative Example B7.

Test Example B2

The pharmaceutical compositions obtained by the methods of Examples B2 and B3 and Comparative B5 to B7 (approximately 250 mg each) were each collected into a brown sample bottle, and were then preserved under light-shielded conditions at 60° C., in a desiccator, the humidity of which had been adjusted with a saturated cobalt chloride aqueous solution (relative humidity: approximately 49%), while the bottle was uncapped.

The residual amounts of everolitnus 7 days and 14 days after initiation of the preservation test were measured by liquid chromatography (HPLC), and the residual percentages of everolimus at individual time points were then calculated. It is to be noted that the residual percentage was calculated according to the following formula. The results are shown in Table 6.

TABLE 6

| | Residual percentage (%) of everolimus | |
|---|---|---|
| | Value on Day 7 | Value on Day 14 |
| Example B2 | 86 | 83 |
| Example B3 | 89 | 83 |
| Comparative Example B5 | 80 | 61 |
| Comparative Example B6 | 77 | 43 |
| Comparative Example B7 | 71 | 73 |

Also in the case of the pharmaceutical compositions (Examples B2 and B3), in which trehalose and mannitol were used as sugars to which the everolitnus solution was to be added dropwise, after the pharmaceutical compositions had been preserved under light-shielded conditions at 60° C. in a saturated cobalt chloride aqueous solution (relative humidity: approximately 49%), the residual percentage of everolimus in both of the pharmaceutical compositions on Day 14 was found to be 80% or more. On the other and, in the pharmaceutical compositions (Comparative Examples B5 and B6) in which sorbitol and glucose were used, and also in the pharmaceutical compositions in which hydroxypropylmethyl cellulose (hypromellose) as a water-soluble cellulose derivative was used, decomposition of everolitnus progressed rapidly, and 14 days after initiation of the preservation test, approximately 30% to 50% of the everolimus was decomposed. In the pharmaceutical composition of Comparative Example B7, the stability of everolimus was ensured to a certain extent, but the yellowing of this pharmaceutical composition was observed under the preservation conditions of the present test.

From the aforementioned results, it became clear that trehalose and mannitol can also be applied as sugars, to which the everolimus solution is to be added. These sugars are sugars having a critical relative humidity at 25° C. of 95% or more, and thus, it has been suggested that the use of sugars having low absorbency would be important.

Rapamycin or a derivative thereof has physical properties, by which it is easily undergone a chemical change such as oxidation. As such, in order to distribute such rapamycin or a derivative thereof in the form of a pharmaceutical formulation to the market, it is necessary to ensure stability under preservation conditions. It has been elucidated that not only the composition of additives including antioxidants such as BHT, but also the production method thereof greatly influences on the chemical stability of the rapamycin or a derivative thereof. That is to say, it was found that a pharmaceutical composition produced by a method of adding an everolimus solution to sugars having a critical relative humidity at 25° C. of 95% or more improves the stability of everolimus.

The pharmaceutical composition according to the present invention is ensured to comprise an active ingredient capable of expressing medicinal effects, and also, the present pharmaceutical composition can prevent the expression of side effects that would be caused by decomposition products. Therefore, it has been demonstrated that the present invention can provide a pharmaceutical formulation, in which the stability of an active ingredient such as everolimus is high and safety is also high.

The invention claimed is:

1. A method for producing a stabilized pharmaceutical composition comprising rapamycin or a derivative thereof, which comprises preparing a solution comprising (A) rapamycin or a derivative thereof, and adding the solution to (B) trehalose, and optionally an antioxidant is dissolved, and then removing the solvent from the solution.

2. A method for producing a stabilized pharmaceutical composition comprising rapamycin or a derivative thereof, which comprises preparing a solution comprising (A) rapamycin or a derivative thereof, and adding the solution to (B) trehalose, and optionally an antioxidant is dissolved, then adding a cellulose derivative and/or sugars to the prepared solution to form a state of suspension, and then removing the solvent from the mixture.

3. A method for producing a stabilized pharmaceutical composition comprising rapamycin or a derivative thereof, which comprises preparing a solution comprising (A) rapamycin or a derivative thereof, and adding the solution to (B) trehalose, and optionally an antioxidant is dissolved, then removing the solvent from the prepared solution to obtain a pharmaceutical composition comprising the rapamycin or a derivative thereof, and then adding a cellulose derivative and/or sugars to the pharmaceutical composition.

4. The method for producing a pharmaceutical composition according to claim 1, wherein the pharmaceutical composition comprises 0.1 to 100.0 parts by mass of (B) the trehalose, based on 1 part by mass of (A) the rapamycin or a derivative thereof.

5. The method for producing a pharmaceutical composition according to claim 2, wherein the pharmaceutical composition comprises 0.1 to 100.0 parts by mass of (B) the trehalose, based on 1 part by mass of (A) the rapamycin or a derivative thereof.

6. The method for producing a pharmaceutical composition according to claim 3, wherein the pharmaceutical composition comprises 0.1 to 100.0 parts by mass of (B) the trehalose, based on 1 part by mass of (A) the rapamycin or a derivative thereof.

7. The method for producing a pharmaceutical composition according to claim 1, wherein the pharmaceutical composition further comprises an antioxidant.

8. The method for producing a pharmaceutical composition according to claim 2, wherein the pharmaceutical composition further comprises an antioxidant.

9. The method for producing a pharmaceutical composition according to claim 3, wherein the pharmaceutical composition further comprises an antioxidant.

* * * * *